United States Patent [19]
Sauer et al.

[11] Patent Number: 5,669,917
[45] Date of Patent: Sep. 23, 1997

[54] SURGICAL CRIMPING DEVICE AND METHOD OF USE

[75] Inventors: Jude S. Sauer, Pittsford; Louis N. Rapp, Dansville; Thomas A. Tiberio, Rochester, all of N.Y.

[73] Assignee: LaserSurge, Inc., Rochester, N.Y.

[21] Appl. No.: 440,403

[22] Filed: May 12, 1995

Related U.S. Application Data

[62] Division of Ser. No. 201,864, Feb. 24, 1994.

[51] Int. Cl.⁶ ............................................. A61B 17/10
[52] U.S. Cl. ................................... 606/139; 606/232
[58] Field of Search .......................... 606/139, 147, 606/232, 69, 73, 75, 148, 151, 157, 158; 29/282, 751, 816

[56] References Cited

U.S. PATENT DOCUMENTS

| | | |
|---|---|---|
| 3,664,345 | 5/1972 | Dabbs et al. . |
| 3,753,438 | 8/1973 | Wood et al. . |
| 3,910,281 | 10/1975 | Kletschka et al. . |
| 3,976,079 | 8/1976 | Samuels et al. . |
| 4,173,067 | 11/1979 | Steiner et al. . |
| 4,201,314 | 5/1980 | Samuels . |
| 4,291,698 | 9/1981 | Fuchs et al. . |
| 4,705,040 | 11/1987 | Mueller et al. . |
| 4,950,285 | 8/1990 | Wilk . |
| 4,953,384 | 9/1990 | Baillet et al. . |
| 4,955,913 | 9/1990 | Robinson . |
| 5,009,663 | 4/1991 | Broome . |
| 5,053,047 | 10/1991 | Yoon . |
| 5,074,874 | 12/1991 | Yoon et al. . |
| 5,078,731 | 1/1992 | Hayhurst . |
| 5,085,661 | 2/1992 | Moss . |
| 5,105,648 | 4/1992 | Steiner et al. . |
| 5,111,681 | 5/1992 | Yasui et al. . |
| 5,116,340 | 5/1992 | Songer et al. ............ 606/103 |
| 5,123,913 | 6/1992 | Wilk et al. . |
| 5,160,339 | 11/1992 | Chen et al. . |
| 5,163,945 | 11/1992 | Ortiz et al. . |
| 5,219,359 | 6/1993 | McQuilkin et al. . |
| 5,274,903 | 1/1994 | Grois et al. . |
| 5,403,348 | 4/1995 | Bonutti ..................... 606/139 |
| 5,405,354 | 4/1995 | Sarrett . |
| 5,423,860 | 6/1995 | Lizardi et al. . |

FOREIGN PATENT DOCUMENTS

| | | |
|---|---|---|
| 2682867 | 10/1991 | France . |
| WO9314701 | 1/1992 | WIPO . |

*Primary Examiner*—Michael Buiz
*Assistant Examiner*—Mark S. Leonardo

[57] ABSTRACT

A surgical apparatus and method of use for maintaining tension upon a length of suture material extending from body tissue is provided. The surgical apparatus deforms and compresses a securing member about a length of suture material which is received therethrough so as to maintain a prescribed amount of tension on the suture material which extends from body tissue and is engaged in the compressed securing member.

7 Claims, 7 Drawing Sheets

SURGICAL CRIMPING DEVICE AND METHOD OF USE

This is a divisional of U.S. application Ser. No. 08/201,864 filed Feb. 24, 1994.

BACKGROUND OF THE INVENTION

1. Field of the Invention

The subject invention relates to endoscopic and laparoscopic surgical instruments, and more particularly to a surgical device for deforming a securing member upon suture material.

2. Description of the Related Art

The recent advancement of minimally-invasive surgical procedures has proven to be an advantageous alternative over prior invasive surgical procedures. Advantages gained by minimally-invasive surgical procedures include quicker recovery time as well as the reduction in the length of hospital stays and medical costs.

Minimally-invasive procedures are typically performed endoscopically through trocar sleeves or cannulas. Prior to introducing the cannula through the body wall, the surgeon insufflates the body cavity with carbon dioxide, e.g., through a Verres needle or like device. Insufflation creates a free area between internal body organs and the body wall. The surgeon then introduces one or more trocars through the body wall into the insufflated body cavity to create a port of entry for accessory instrumentation. For example, graspers, dissectors, clip appliers, lasers and electrocautery devices are routinely employed endoscopically with the visual assistance of an endoscope and an external television monitor.

However, a difficulty which arises during endoscopic surgery is the procedure of knotting suture material so as to bring tissue pieces together. The surgeon must pass the ends of a piece of suture material through the tissue pieces which were desired to be adjoined. The surgeon would then pull on the suture material, thereby tensioning the suture material so as to effectively bring the tissue pieces together. The surgeon would maintain this tension upon the length of suture material by placing a knot in the suture material. This placement of the knot in the suture material during endoscopic surgery is both time consuming and burdensome due to the difficult maneuvers and manipulation which is required by the surgeon through the restrictive entry areas of the trocar sleeves or cannulas.

There have been many prior art attempts to circumvent the need for the knotting of suture material so as to maintain a desired tension upon suture material extending from body tissue. However, such prior art devices have essentially been staples, clips, clamps or other fasteners not providing the adjustable tension obtained by the surgeon while knotting a length of suture material; U.S. Pat. No. 5,041,127 to Hayhurst et al., No. 5,080,663 to Mills et al., No. 5,021,059 to Kensy et al., No. 4,841,888 to Mills et al., No. 4,741,330 to Hayhurst, No. 4,724,840 to McVay et al., No. 4,705,040 to Mueller et al., No. 4,669,473 to Richards et al., No. 4,627,437 to Bedi et al., No. 4,448,194 to DiGiovanni et al., No. 4,039,078 to Bone, No. 4,235,238 to Ogiv et al., No. 4,006,747 to Kronenthal et al., No. 3,875,648 to Bone and No. 5,085,661 to Moss are representative of such prior art devices for use in place of conventional suturing. However, none of the above listed devices overcome the disadvantages associated with knotting suture material so as to maintain a prescribed amount of tension upon the suture material so as to adjoin tissue pieces together.

Therefore, it is advantageous to provide a new surgical device and method for endoscopically providing adjustable tension upon a length of suture material which extends from body tissue.

SUMMARY OF THE INVENTION

The present invention provides a novel surgical apparatus for connecting and securing the ends of a suture loop, and more particularly, for deforming a suture securing or cinch member about a loop of suture material extending from body tissue at an operative site. Briefly, the present invention enables the surgeon to bring about a desired tension upon a length of suture material extending from body tissue and maintain that tension by deforming a securing member upon the suture material, thus replacing the need for knotting the suture material.

The surgical apparatus of the present invention includes a handle portion having a pivotable handle member associated therewith and an elongated body portion extending distally from the handle portion, wherein the elongated body portion defines a longitudinal axis thereof. An atraumatic tool assembly is operatively associated with a distal end portion of the elongated body portion and is remotely operable from the handle portion. In particular, the tool assembly includes a deforming assembly for enclosing and deforming the securing member upon a length of suture material extending from body tissue. Further, the tool assembly may include a cutting member detachably engaged therewith for cutting a length of suture material extending from a deformed securing member.

The deforming assembly includes an anvil portion defined in a distal end portion of the tool assembly and a hammer element dimensioned and configured for movement towards the anvil portion. The distal end portion of the hammer element is further dimensioned and configured so as to deform a securing member releasably disposed in the anvil portion of the tool assembly.

The elongated body portion comprises an endoscopic tubular member having an inner tubular member received therein. A distal end of the inner tubular member is detachably engaged with the cutting member while a proximal end portion of the inner rod member is operatively associated with actuation structure provided in the handle portion for remotely actuating the cutting member therefrom. An inner rod member is slidably received in the inner tubular member wherein a distal end portion of the inner rod is operatively associated with the hammer element disposed in the tool assembly. A proximal end portion of the inner rod member is operatively associated with the pivotable handle member such that movement of the pivotable handle member effects corresponding remote actuation of the hammer element. Actuation of the hammer element effectively deforms the securing member releasably disposed in a distal end portion of the tool assembly.

The actuation structure for actuating the cutting member may include a trigger assembly operatively associated with the handle portion. The trigger assembly includes a trigger arm pivotably mounted to the handle portion and a bias spring operatively associated with the trigger arm and the handle portion for biasing the trigger arm into an open position. Movement of the trigger arm effects corresponding actuation of the cutting member in the tool assembly.

A securing member is releasibly disposed in the anvil portion and in alignment with the hammer element such that coaxial distal movement of the hammer element into the anvil portion of the tool assembly deforms the securing member. The securing member preferably comprises a cylindrical tubular member having opposed first and second ends and a compressible outer surface portion defining an inner bore portion extending between the first and second ends. The inner bore portion is configured for reception of a length of suture material therethrough.

A rotation mechanism may be provided for rotating the endoscopic tubular member and the tool assembly attached thereto about the longitudinal axis defined by the elongated body portion. The rotation mechanism includes an annular collar operably mounted in the handle portion adjacent a proximal end portion of the endoscopic tubular member.

In another embodiment of the present invention, the actuation structure for actuating the cutting member comprises an arm member slidably mounted to the handle portion. Movement of the arm member relative to the handle portion effects corresponding actuation of the cutting member in the tool assembly.

In use, the surgeon places a securing member in the anvil portion defined in the tool assembly. Next, two ends of a suture loop are brought extracorporeally, via a cannula assembly, enabling the surgeon to thread the suture loop ends through the securing member using a conventional threading tool. The surgeon, while grasping the ends of the suture loop threaded through the securing member, inserts the tool assembly and a portion of the endoscopic body portion of the surgical apparatus into the body cavity, via a cannula assembly, into approximation with body tissue having the sutures extending therefrom.

The surgeon then gently pulls on the suture loop ends extending from the body cavity so as to bring the desired tissue pieces together thereby tensioning the suture material extending from the body tissue. The surgeon then pulls the pivotable handle member to compress the securing member into a deformed configuration so as to maintain the suture material extending from the tissue pieces in their tensioned state. In the embodiment having a cutting member, the surgeon then pulls the trigger arm to actuate the cutting member in the tool assembly to cut the unsecured lengths of suture material extending from the compressed securing member, and, thereafter, the deformed securing member is released from the tool assembly. Alternately, a separate cutting member can be used to cut the suture material.

BRIEF DESCRIPTION OF THE DRAWINGS

Further features of the surgical apparatus and method of use of the present invention will become more readily apparent from the following detailed description of the invention taken in conjunction with the accompanying drawings, in which.

DETAILED DESCRIPTION OF THE PREFERRED EMBODIMENTS

The present invention shall be discussed in terms of endoscopic procedures and apparatus which is intended to include laparoscopic procedures.

In the drawings and in the description which follows, the term "proximal" will refer to the end of the surgical apparatus which is closest to the operator, while the term "distal" will refer to the end of the apparatus which is furthest from the operator.

Figure 1:
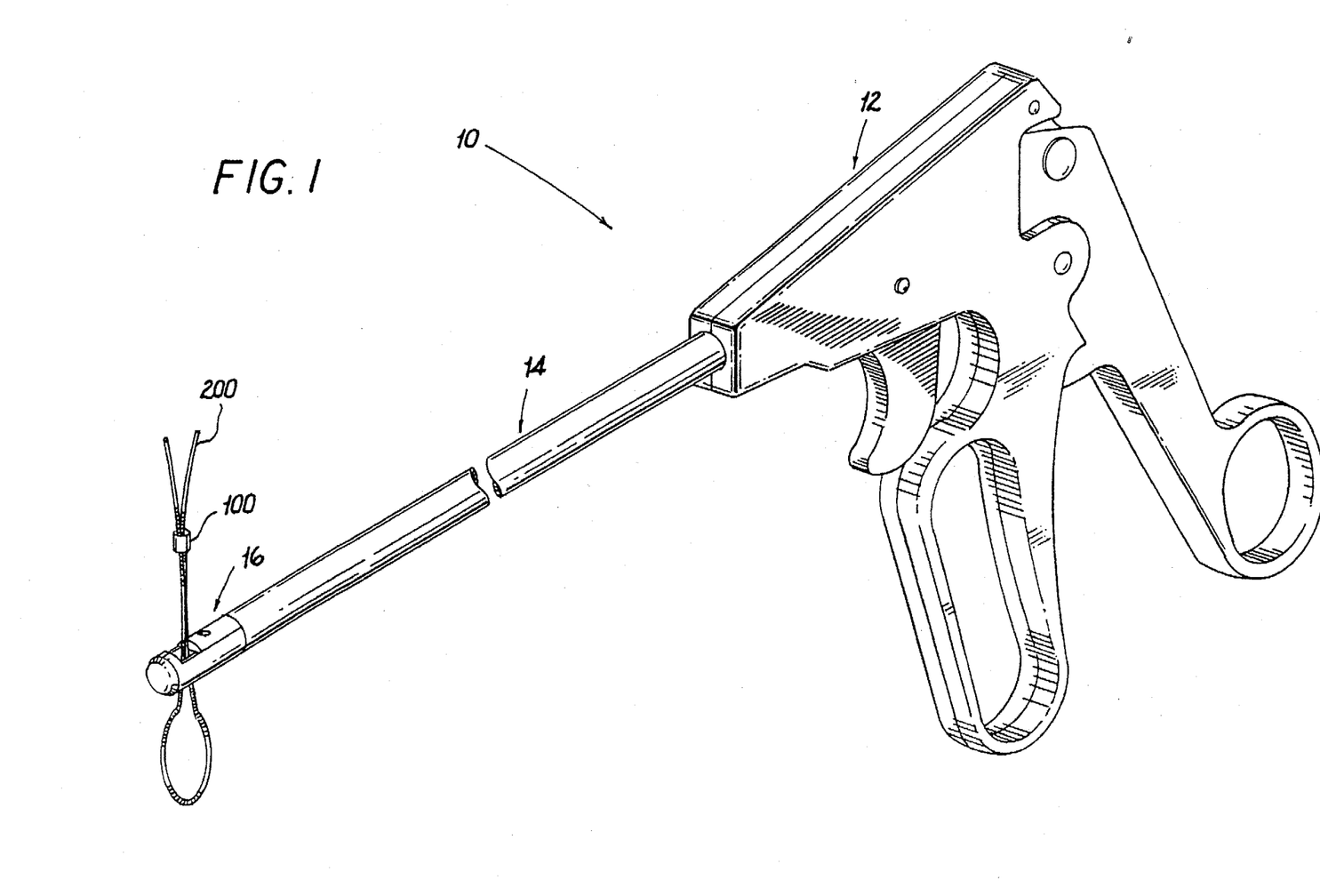
FIG. 1 illustrates a perspective view of a surgical apparatus according to the subject invention.

Referring now in specific detail to the drawings, in which like reference numbers identify similar or identical elements, FIG. 1 illustrates a preferred embodiment of a surgical apparatus, shown generally at 10. The surgical apparatus 10 may comprise a handle portion 12 and an elongated body portion 14 extending distally from the handle portion 12. An atraumatic tool assembly 16 for contacting and deforming a suture securing member 100 to cinch a length of suture material is operatively associated with a distal end portion of the elongated body portion 14 and is remotely operable by the handle portion 12. The embodiment of FIG. 1 is adapted for and particularly useful in endoscopic or laparoscopic procedures wherein at least an endoscopic portion of the surgical apparatus 10 is inserted into the operative site through a cannula device (not shown).

Figure 2:
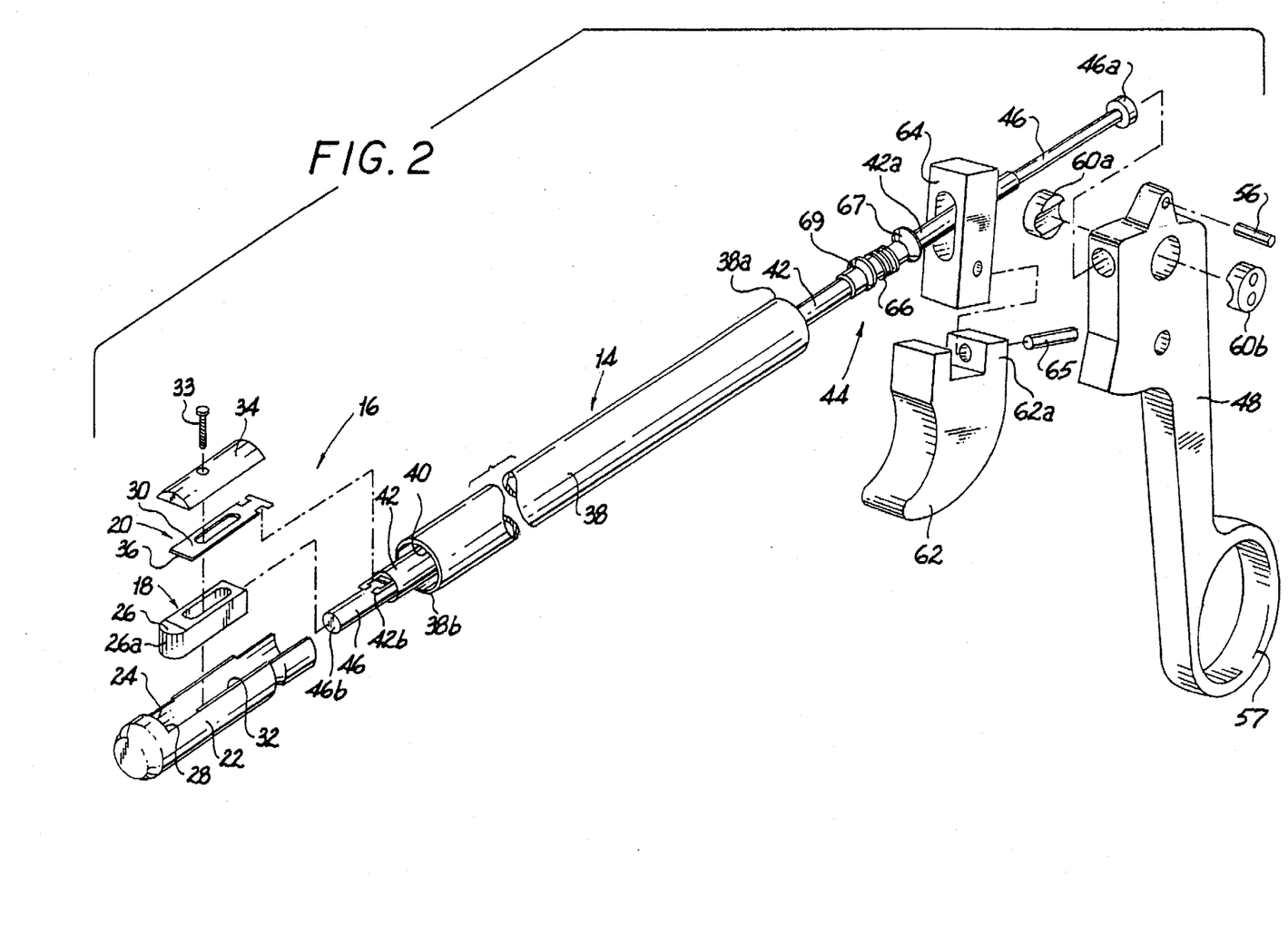
FIG. 2 illustrates an exploded view of the actuation structure of the surgical apparatus of FIG. 1.

Turning to FIG. 2, the tool assembly 16 includes an elongated tool housing portion 22 which defines a central bore 24 extending therethrough. The tool assembly 16 comprises a deforming assembly 18 for deforming securing member 100 (FIG.1) to cinch a length of suture material and a cutting assembly 20 for cutting a length of suture material which extends from a deformed securing member. As will be described in greater detail below, both the deforming assembly 18 and the cutting assembly 20 are remotely operable from the handle portion 12 (FIG. 1).

The deforming assembly 18 includes a hammer element 26 slidably received within the central bore 24 of the housing portion 22. An anvil portion 28 is defined at the distal end portion of the tool housing portion 22 and is in communication with the central bore 24 of the housing portion 22. An aperture 23 (FIG. 5) is formed on the bottom surface of the tool housing 22 in communication with the anvil portion 28 and is dimensioned to receive suture material 200. The hammer element 26 is provided with a substantially rounded distal end 26a which engages the anvil portion 28 and compress a securing member 100 releasably disposed in the anvil portion 28 of the tool housing 22 (FIG. 9) as the hammer element 26 moves into approximation with the anvil portion 28.

Figure 9:
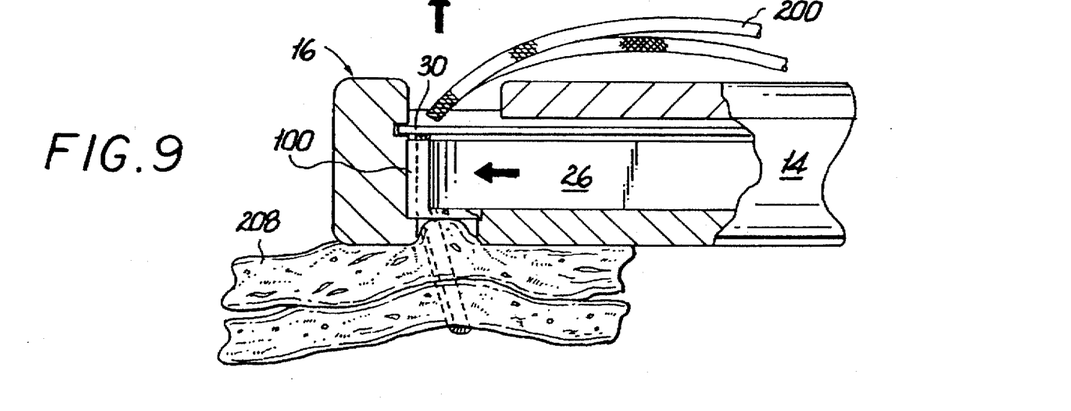
FIG. 9 is a side elevational view in partial cross-section of the tool assemble of the surgical apparatus illustrated in FIG. 8, further illustrating the cutting blade cutting a length of suture material extending from a compressed securing member.

The cutting assembly 20 comprises a cutting blade 30 which moves reciprocally along a cutout portion 32 defined along the top surface of the tool housing 22. The cutting blade 30 engages the distal end 42b of an inner tubular member 42 which is received through the elongated body portion 14 (FIG. 2). A threaded screw 33 mounts a blade cover 34 atop the cutout portion 32 of the tool housing 22 to enclose the cutting blade 30 within the tool assembly 16. A distal end of the cutting blade 30 is provided with a sharpened edge 36 for severing suture material 200 which extends from a securing member 100 disposed in the anvil portion 28 of the tool assembly 18 (FIG. 9).

Figure 3:
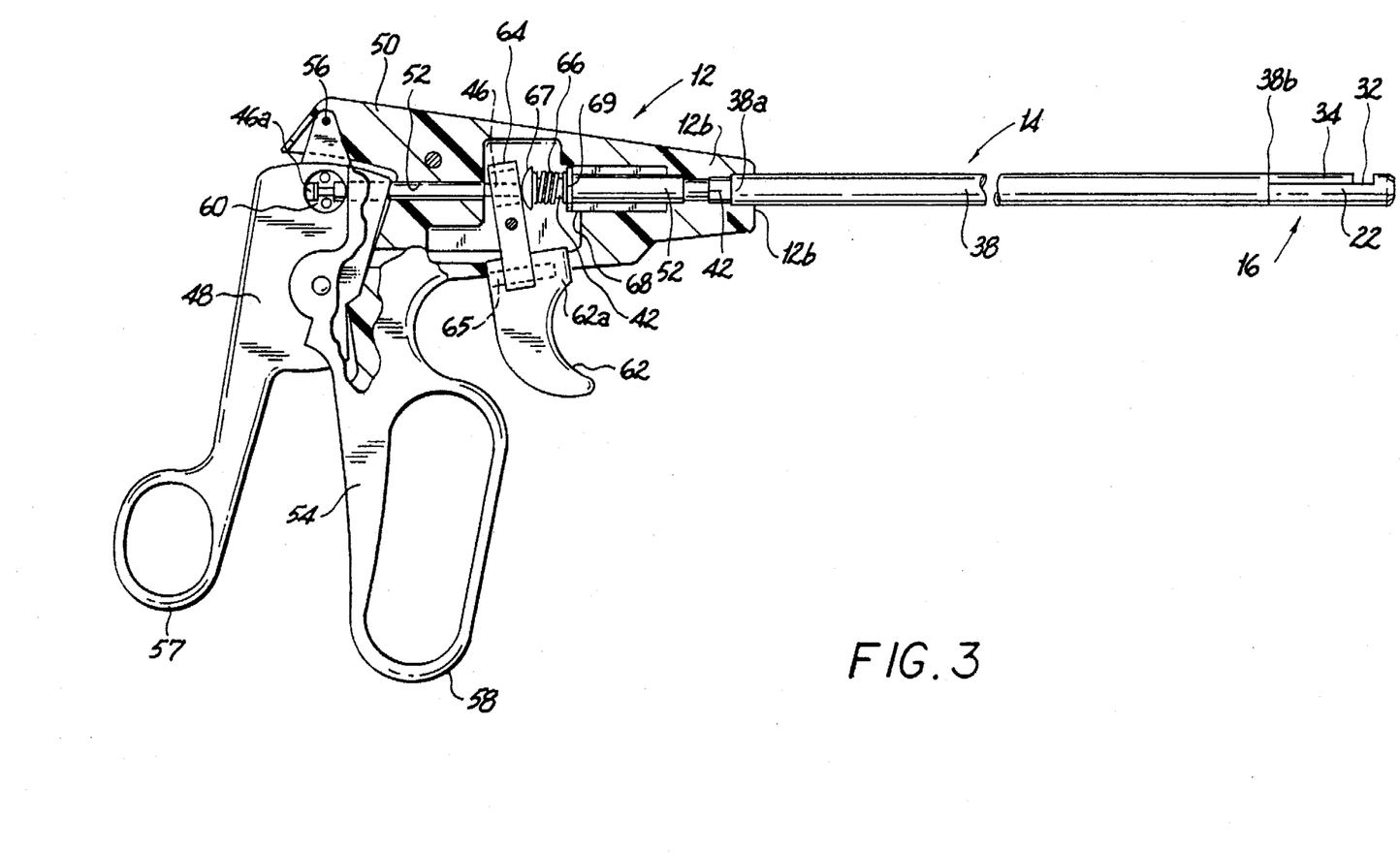
FIG. 3 is a side elevational view in partial cross-section of the surgical apparatus of FIG. 1.

Referring now to FIGS. 2 and 3, the elongated body portion 14 includes an endoscopic tubular member 38 attached at its proximal end 38a to the handle portion 12 and at a distal end 38b to the tool housing 22. The endoscopic tubular member 38 defines a central bore 40 therethrough which is aligned and in communication with the central bore 24 of the tool housing 22. An inner tubular member 42 is slidably received in the central bore 40 of the endoscopic tubular member 38 and is adapted for coaxial motion therein. As mentioned above, the distal end portion 42b of the inner tubular member 42 is connected to the cutting blade 30 while the proximal end portion 42a of the inner tubular member 42 is attached to actuation structure 44 operatively associated with the handle portion 12.

An inner rod member 46 is slidably received in the inner tubular member 42 and is adapted for coaxial motion therein. A distal end 46b of the inner rod member 46 attaches to the hammer element 26, while a proximal end 46a of the inner rod member 46 is operatively associated with a pivotable handle member 48 in the handle portion 12, the connection of which will be discussed in greater detail below.

Still referring in FIGS. 2 and 3, the handle portion 12 includes a body portion 50 defining a bore 52 extending from a distal end 12b thereof. The body portion 50 of the handle portion 12 defines a stationary grip member 54 and includes the pivotable handle member 48 which is pivotably connected to the body portion 50 about the pivot pin 56, so as to be pivotably movable towards stationary grip member 54. Finger loops 57, 58 are provided on the lower ends of handle member 48 and grip member 54, respectively. Clearly, other handle configurations are contemplated.

A pivot bushing 60 is mounted in the pivoting handle member 48 and comprises halve sections 60a and 60b which capture a proximal end 46a of the inner rod member 46 to control axial motion thereof. The pivot bushing 60 retains the proximal end 46a of the inner rod member 46 to freely rotate therein and maintains the inner rod member 46 in axial alignment with the inner tubular member 42 throughout the entire range of motion of pivoting handle member 48. Thus, movement of pivoting handle member 48 into approximation with the stationary grip member 54 causes the inner rod member 46 to coaxially move in a distal direction relative to the handle portion 12 so as to effect distal movement and acutation of the hammer element 26 in the tool assembly 16.

With continuing reference to FIGS. 2 and 3, the actuation structure 44 for remotely actuating the cutting blade 30 in the tool assembly 18 comprises a trigger arm 62 pivotable mounted to the body portion 50 of the handle portion 12. A linkage member 64 attaches to the top portion 62a of the trigger arm 62 by connecting pin 65, wherein an annular flange member 67 mounts to the outer surface portion of the inner tubular member 42 so as to abut against the linkage member 64. A grommet 69 is received about the inner tubular member 42 distally from the annular flange member 67. A compression spring 66 is received about the inner tubular member 42 intermediate the grommet 69 and the annular flange member 67. As best shown in FIG. 3, the grommet 69 abuts against a retaining wall 68 formed in the body portion 50 of the handle portion 12, wherein the compression spring 66 biases against the grommet 69 so as to effect the compression spring 66 to bias against the flange member 67 which forces the trigger arm 62, via the linkage member 64, to bias into an open position (FIG. 3) when the trigger arm 62 is approximated towards the stationary grip member 58. Thus, proximal movement of the trigger arm member 62 moves the inner tubular member 42 coaxially in a distal direction relative to the handle portion 12 to actuate the cutting blade 30 in the tool assembly 16.

Figures 5, 6:
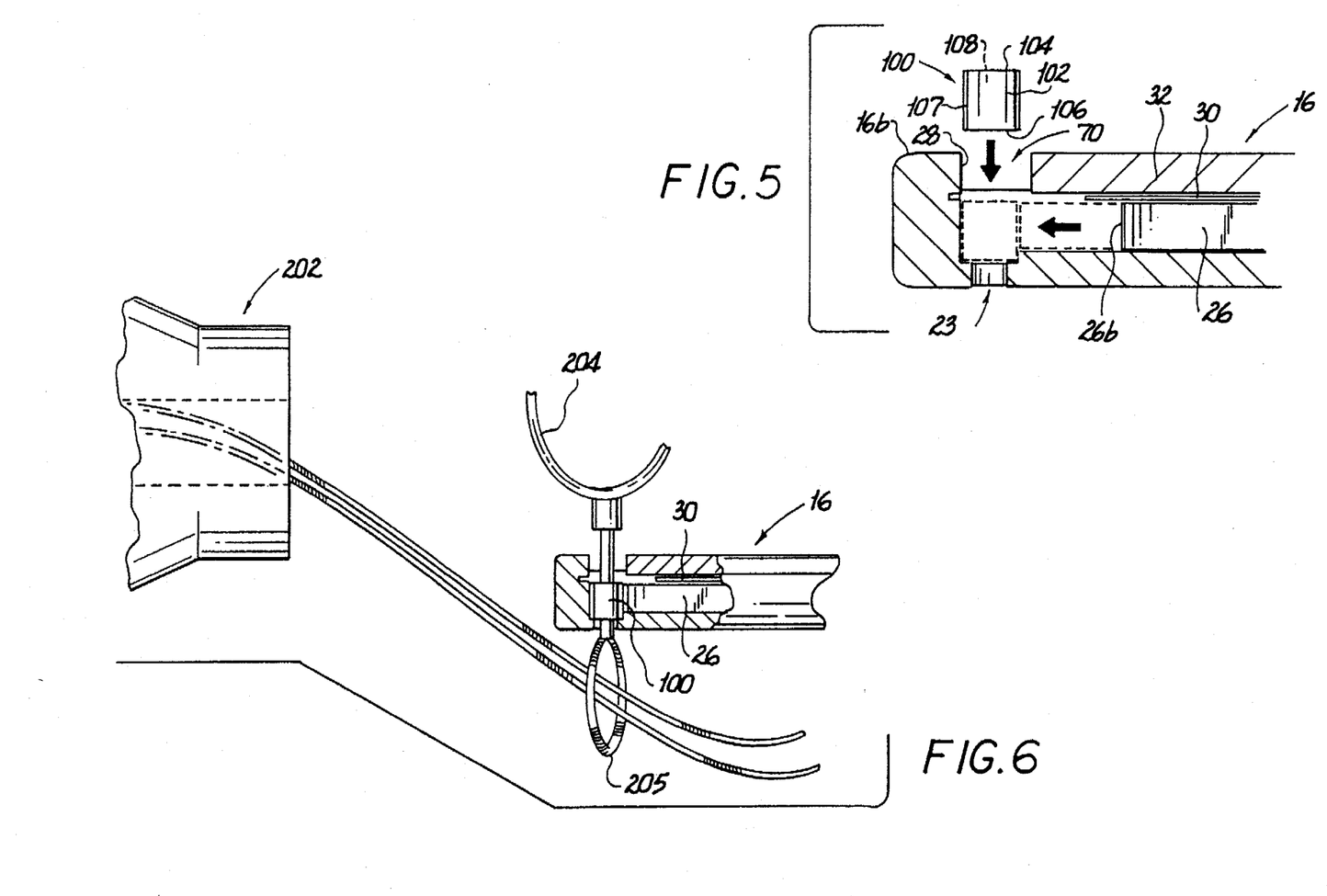
FIG. 5 is a cross-sectional view of the tool assembly of the surgical apparatus of FIG. 1 illustrating the insertion of a securing member into the tool assembly.
FIG. 6 is a side elevational view in partial cross-section of the tool assembly illustrated in FIG. 1, wherein a threading device is shown capturing a suture for engagement in the securing member.

Referring to FIG. 5, the securing member 100 for securing the suture as will be described below comprises a cylindrical member 102 having first and second opposed ends 104, 106, although other configurations are contemplated. The securing member 100 includes an outer compressible surface 107 defining an inner bore 108 extending between the opposed first and second ends 104, 106. The securing member 100 is placed adjacent the anvil portion 28 in the tool assembly 16 through the opening 70 provided intermediate the distal end 16b of the tool assembly 16 and the blade cover 30 disposed along the top surface of the cutout portion 32 of the tool assembly 16.

The securing member 100 is fabricated from a deformable biocompatible material and is preferably formed of a non-bioabsorbable material. Alternatively, the securing member 100 may be fabricated from a bioabsorbable polymer such as a homopolymer, copolymer or a blend obtained from one or more monomers selected from the group consisting of glycolic acid, lactide, lactic acid, p-dioxanone, E-caprolactone and trimethylene carbonate.

Figure 4:
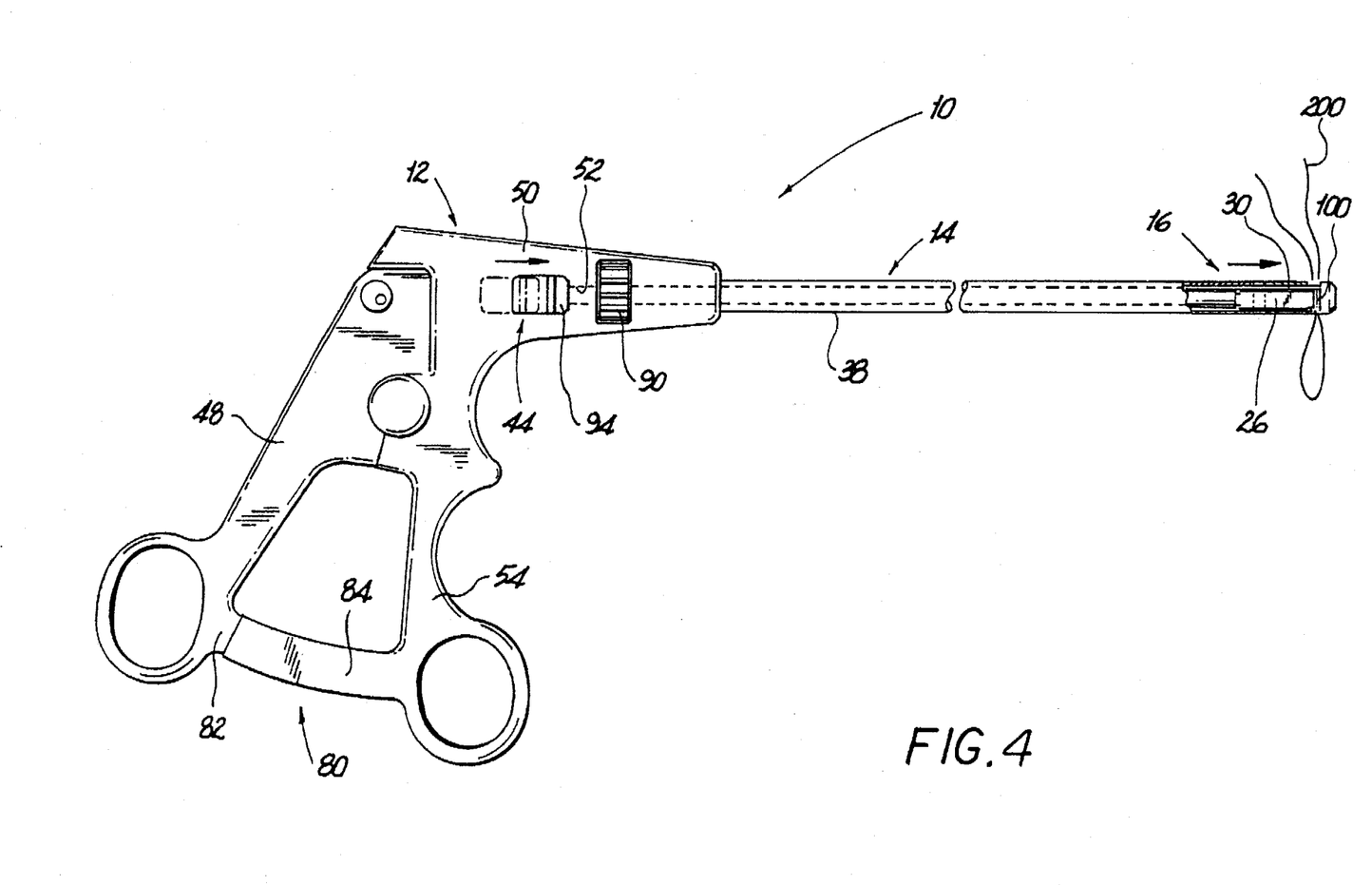
FIG. 4 is a side elevational view of another embodiment of the surgical apparatus according to the subject invention.

Another embodiment of the surgical apparatus 10 of the present invention is illustrated in FIG. 4. In this embodiment, an interengaging ratchet mechanism 80 is provided to incrementally adjust and hold the position of the pivotable handle member 48. This incremental positioning, which sets the pivotable handle member 48 at various locations along its path of travel, provides a means to incrementally actuate the hammer element 26 during a surgical procedure. The ratchet mechanism 80 includes interengaging racks 82, 84 which are respectively provided on the handle members 48 and 54. Alternately, ratchet mechanism 80 can be positioned internally within the body portion 50 of the handle portion 12 so that the mechanism is not exposed.

In the embodiment illustrated in FIG. 4, the endoscopic tubular member 38 and the tool assembly 16 attached thereto are axially rotatable by a rotation knob 90 mounted in the body portion 50 of the handle portion 12. The rotation knob 90 engages a bushing (not shown) attached to a proximal end portion of the endoscopic tubular member 38. The rotation knob 90 is preferably knurled or provided with ridges to allow for easy manipulation by the surgeon's thumb or fingers. Additionally, the bushing may be provided with angular faces of polygonal cross-section cooperating with corresponding races formed in the body portion 50 of the handle portion 12 so as to provide predetermined rotational stops such that the tool assembly 16 is maintained at a given angular orientation relative to the handle assembly 12.

Moreover, in the embodiment illustrated in FIG. 4, the actuation structure 44 for remotely actuating the cutting blade 30 in the tool assemble 16 comprises an arm member 94 slidably mounted to the body portion 50 of the handle portion 12. The slidable arm member 94 engages with a proximal end portion of the inner tubular member 42 in the central bore 52 of the body portion 50 of the handle portion 12, thus, the distal movement of the slidable arm member 94 effects corresponding proximal movement of the cutting blade 30 in the tool assembly.

Figure 7:
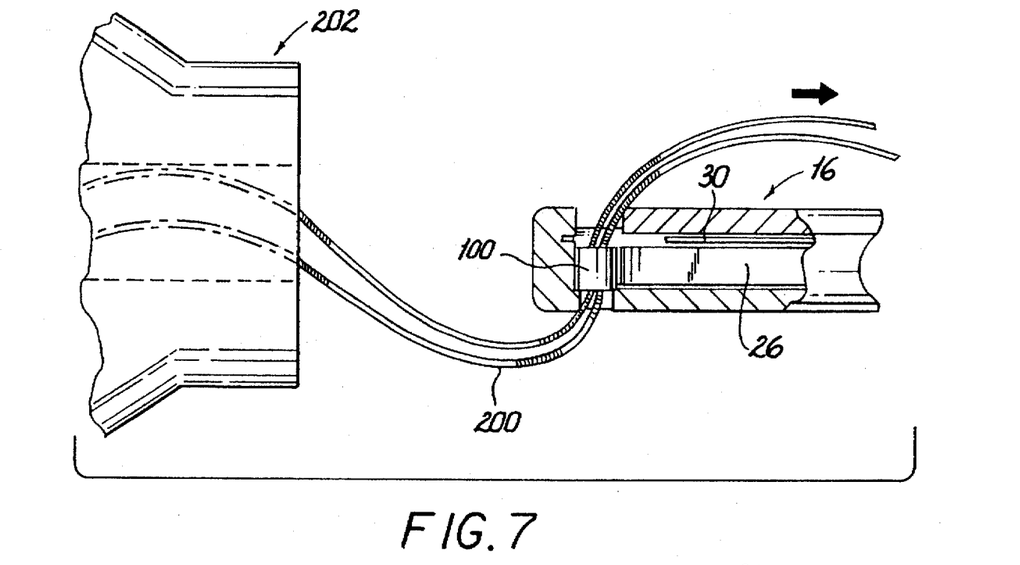
FIG. 7 is a side elevational view in partial cross-section of the tool assembly illustrated in FIG. 1, wherein suture material is positioned with in the securing member.

Referring now to FIGS. 5–9, in use to secure the suture to body tissue through which it has been placed, i.e., to maintain tension on the suture without tying a knot, the surgeon squeezes handle 12, pulling pivoting handle member 48 towards stationary grip member 57, thereby pulling hammer element 28 back so as to make space to insert securing member 100 into spact 70 adjacent hammer element 28 of the tool assembly 16, as shown in FIG. 5 in phantom. Turning now to FIGS. 6 and 7, the surgeon next moves the two ends of a suture 200 extracorporeally (i.e., outside the body), via a cannula assembly 202 (FIG. 6) and threads the ends of the suture 200 through aperture 23 in tool housing 22 and through the securing member 100 releasably disposed in the tool assembly 16 using a conventional threading tool 204 (FIG. 6). Such conventional threading tools may have a flexible loop 205 through which the thread or suture may be placed. When the tool 204 is drawn through securing member 100, flexible loop 205 compresses to fit through securing member 100, pulling the two suture ends with it. Threading tool 204 can be modified so that threading can be accomplished intracorporeally.

Figure 8:
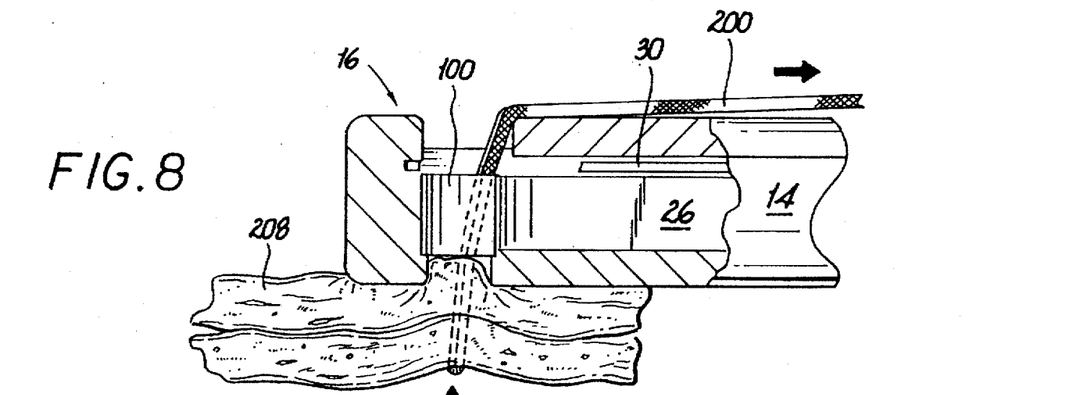
FIG. 8 is a side elevational view in partial cross-section of the tool assembly of the surgical apparatus adjacent body tissue wherein suture material is positioned in the securing member.
Figure 10:
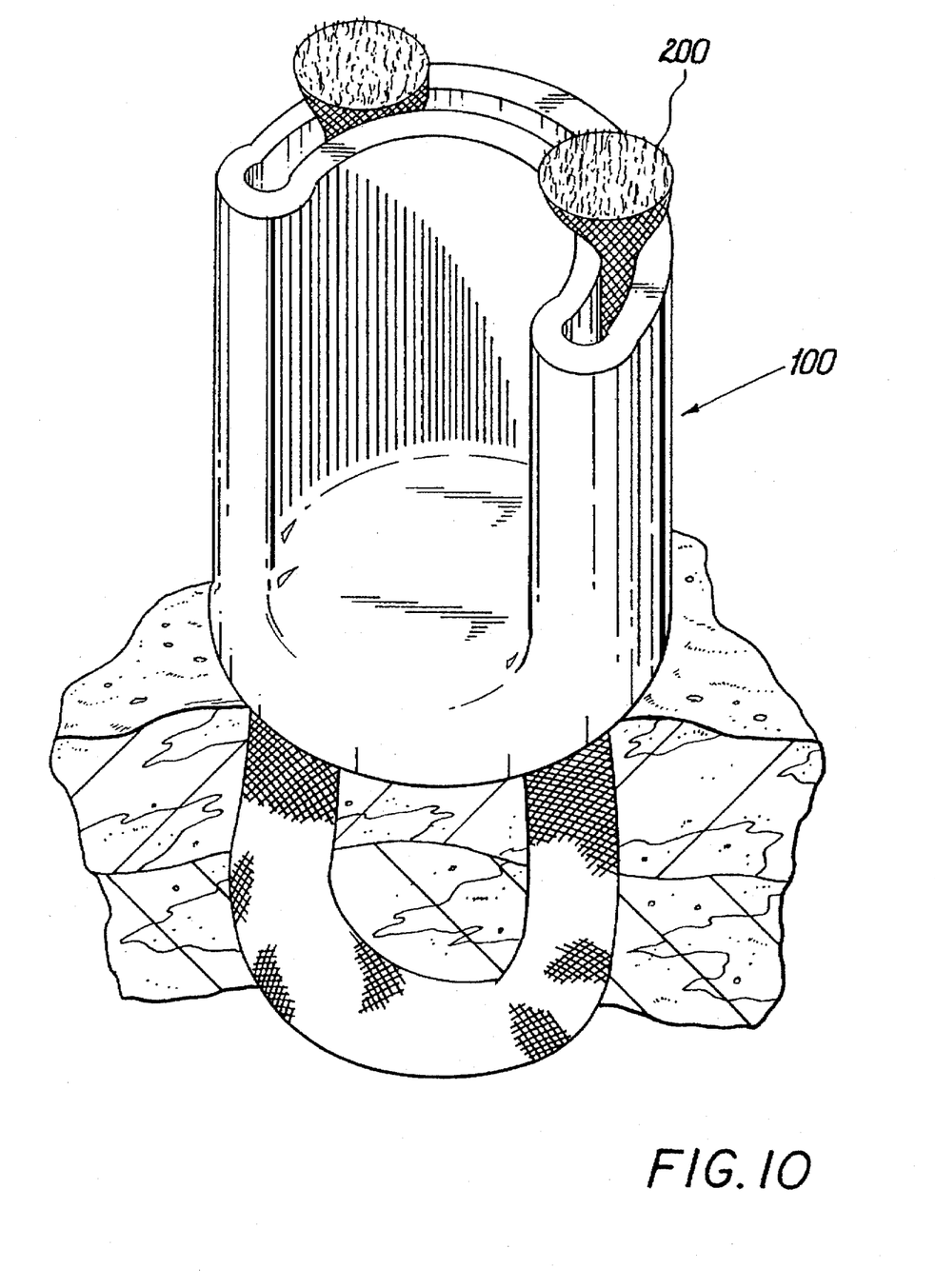
FIG. 10 is an enlarged view of the suture securing member shown deformed around two ends of a suture.

Thereafter, the surgeon, while grasping the ends of the suture 200 threaded through the securing member 100, inserts the tool assembly 16 (and the elongated body portion 14) into the body cavity via a cannula assembly 202, and into approximation with the body tissue 208 having the two ends of suture 200 extending therefrom (FIG. 8). The surgeon then gently pulls proximally on the suture ends 200 extending from the body cavity while cinching securing member 100 down upon suture ends 200 so as to bring the tissue pieces 208 together (FIG. 8), therein tensioning the suture 200 extending from the body tissue 208. The surgeon then further actuates the pivotable handle member 48 to enclose, compress and deform the securing member 100 about the suture 200 extending therethrough, thus changing the original larger dimension of the bore of the securing member to a smaller-dimensioned bore that catches and holds suture ends 200. See FIG. 10. In one embodiment, the securing member starts out as a cylinder and is made of a compressible material so that upon compression, the C-shaped securing member of FIG. 10 results. This maintains the suture 200 in its present tensioned state. Thus, tension is maintained on the suture without the difficult and time-consuming task of tying a knot.

Referring to FIG. 8, actuation of the trigger arm 62 effectuates the cutting blade 30 in the tool assembly 16 to cut the unsecured lengths of suture 200 extending from the compressed securing member 100. After full actuation of the trigger arm 62, the trigger arm 62 if returned to its initial rest position as described above, thereby retracting cutting blade 30 to its original position. In the embodiment of the instrument not having a cutting member, the surgeon utilizes a separate cutting element, e.g., endoscopic scissors, to remove the excess suture.

The surgeon then removes the tool assembly 16 from the body cavity, via a cannula device 202, and the surgeon is then enabled to insert a new securing member 100 in the tool assembly 16 so as to repeat the above described procedure.

Although the above description relates to suture placed in an endoscopic loop in the body cavity, this device may be used to crimp suture in any situation where it is indicated.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A suture securing member comprising a first end portion, a second end portion and a bore having a first dimension and extending from said first end portion to said second end portion, said bore dimensioned to receive a length of suture material so that the suture material extends through said first and second end portions, said securing member being comprised of compressible material so that upon compression of said securing member the size of said bore is reduced to a second smaller dimension to thereby cinch the suture material to maintain tension therein.

2. A suture securing member as recited to claim 1, wherein said securing member is substantially cylindrical in configuration prior to compression.

3. A suture securing member as recited in claim 1, wherein said securing member is C-shaped in configuration after compression.

4. A method of applying a securing member having an outer compressible surface to a length of suture material comprising the steps of;

a) threading the length of suture material through said securing member;

b) positioning said securing member so as to achieve sufficient tension required of the length of suture material to suture body tissue; and c) compressing said securing member upon said length of suture material so as to maintain a desired tension upon said length of suture material between said securing member and the body tissue.

5. A method of securing sutures as recited in claim 4, further comprising the step of cutting a length of unsecured suture material which extends from a compressed securing member.

6. A method of securing sutures as recited in claim 4, wherein the threading step includes threading at least one cut end of a loop of suture material through said securing member.

7. A method of securing sutures as recited in claim 4, wherein said securing member comprises a cylindrical member having opposed first and second ends defining an inner bore portion extending between said first and second ends.

* * * * *